(12) United States Patent
Bates et al.

(10) Patent No.: US 7,691,140 B2
(45) Date of Patent: Apr. 6, 2010

(54) ANASTOMOSIS DEVICE FOR VASCULAR ACCESS

(75) Inventors: Brian L. Bates, Bloomington, IN (US); Clay D. Fette, Lebanon, IN (US); Ram H. Paul, Jr., Bloomington, IN (US); Paul D. Amarant, Bloomington, IN (US)

(73) Assignees: Cook Incorporated, Bloomington, IN (US); Cook Biotech Incorporated, West Lafayette, IN (US)

( * ) Notice: Subject to any disclaimer, the term of this patent is extended or adjusted under 35 U.S.C. 154(b) by 664 days.

(21) Appl. No.: 10/843,816

(22) Filed: May 12, 2004

(65) Prior Publication Data

US 2005/0038455 A1 Feb. 17, 2005

Related U.S. Application Data

(60) Provisional application No. 60/469,708, filed on May 12, 2003.

(51) Int. Cl.
*A61F 2/06* (2006.01)
(52) U.S. Cl. ..................................... 623/1.13; 623/1.14
(58) Field of Classification Search ................. 623/1.13, 623/1.36, 23.72, 1.12, 1.14, 1.15, 1.16, 1.18; 606/8, 153–156
See application file for complete search history.

(56) References Cited

U.S. PATENT DOCUMENTS

| | | | | |
|---|---|---|---|---|
| 5,749,880 A | * | 5/1998 | Banas et al. | 606/198 |
| 5,755,778 A | * | 5/1998 | Kleshinski | 623/1.13 |
| 6,440,163 B1 | * | 8/2002 | Swanson et al. | 623/1.23 |
| 6,451,048 B1 | | 9/2002 | Berg et al. | |
| 6,485,513 B1 | * | 11/2002 | Fan | 623/1.36 |
| 6,638,312 B2 | * | 10/2003 | Plouhar et al. | 623/23.72 |
| 6,695,833 B1 | * | 2/2004 | Frantzen | 623/1.13 |
| 6,699,263 B2 | * | 3/2004 | Cope | 606/232 |
| 6,746,480 B2 | * | 6/2004 | Scholz et al. | 623/1.31 |
| 6,818,016 B1 | * | 11/2004 | Nabel et al. | 623/1.42 |
| 6,908,624 B2 | * | 6/2005 | Hossainy et al. | 424/424 |
| 7,175,652 B2 | * | 2/2007 | Cook et al. | 623/1.13 |
| 2005/0049675 A1 | | 3/2005 | Wallace | |

* cited by examiner

*Primary Examiner*—Todd E Manahan
*Assistant Examiner*—Michael G Mendoza
(74) *Attorney, Agent, or Firm*—Richard J. Godlewski

(57) ABSTRACT

An anastomosis device (12) for advantageously bridging an artery and a vein. The anastomosis device includes a tubular graft (15) with first and second ends (47 and 48) and a longitudinal passageway extending longitudinally through the graft. The device further includes a first stent (10) disposed about the first end of the tubular graft and a second stent (10) disposed about the second end of the tubular graft. Each of the first and second stents has a plurality of hooks or barbs (11) pointed or releasable to the point toward the other end of the graft.

3 Claims, 7 Drawing Sheets

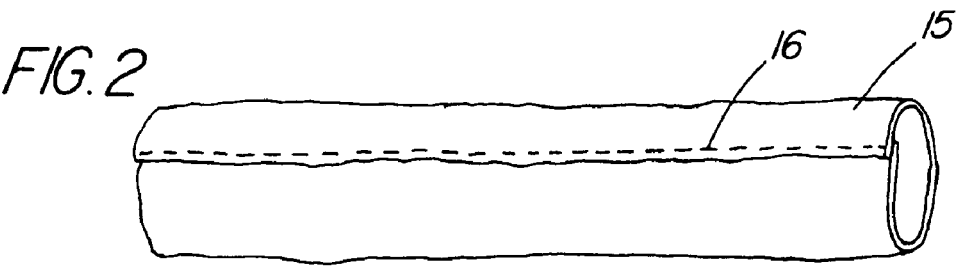
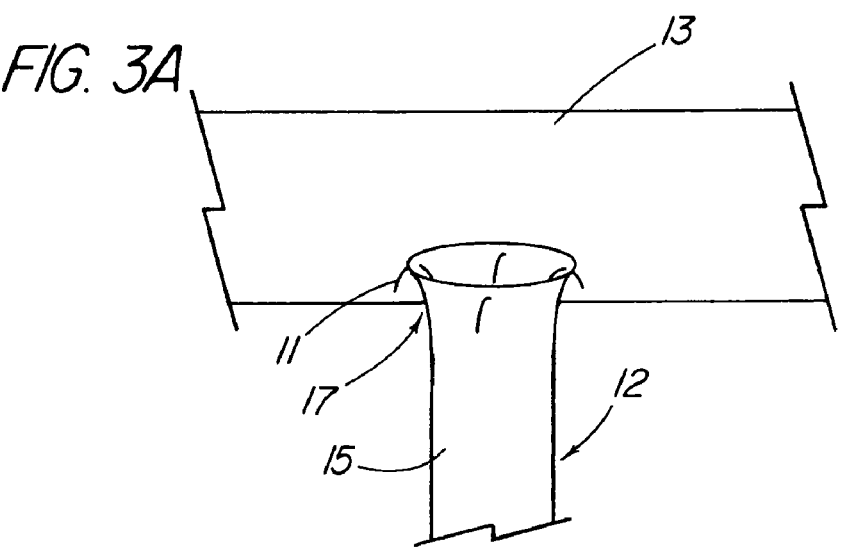
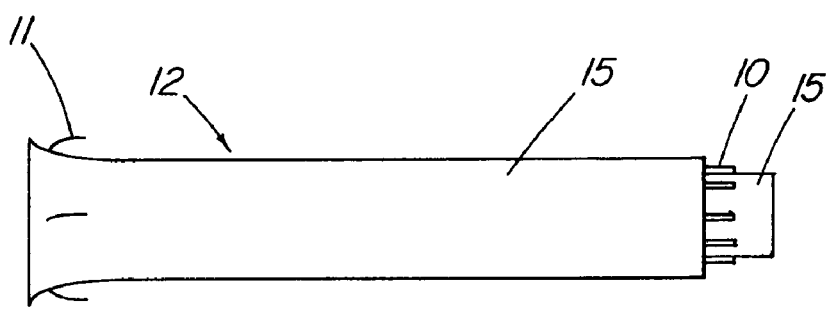
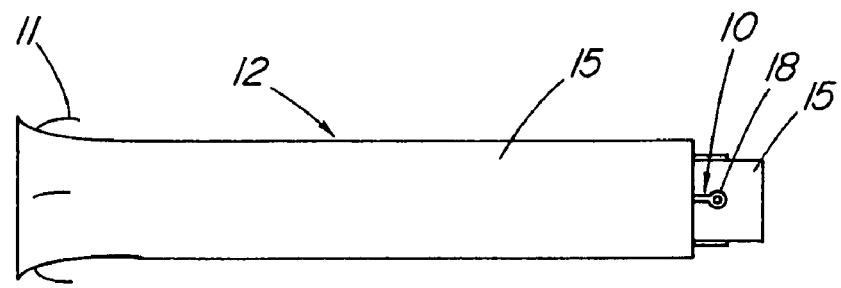

US 7,691,140 B2

ANASTOMOSIS DEVICE FOR VASCULAR ACCESS

CROSS-REFERENCE TO RELATED APPLICATIONS

This application claims priority of provisional application Ser. No. 60/469,708, filed May 12, 2003.

TECHNICAL FIELD

The present invention relates to the field of medical devices and, in particular, an anastomosis device and method of use therefore.

BACKGROUND OF THE INVENTION

Current devices and techniques exist which allow for open surgical attachment of an artery to a vein for vascular access or replacement of diseased vessels. This includes sewing in a graft between the internal mammary artery and a coronary vessel, the radial artery and cephalic vein, the brachial artery and cephalic vein, the brachial artery and basilica vein, the ulnar artery and basilica vein, the brachial artery to branches of the antecubital vein, and a saphenous vein loop fistula. To our knowledge, no known non-invasive methods or devices exist that employ non-invasive catheter delivery of an anastomosis device for access between these areas. Prior to using synthetic grafts, the radiologist or nephrologist's first choice is a naturally occurring vessel to act as an AV fistula for vascular access. Only after determining their inadequacy is a synthetic vessel or exogenous vessel (e.g., animal derived small intestine submucosa (SIS)) used.

SUMMARY OF THE INVENTION

The present invention is directed to an illustrative minimally invasive anastomosis device for advantageously bridging an artery and a vein. The device is loaded into a sheath or introducer system and pushed out over a wire to the desired location following the commonly used Seldinger technique, but with ultrasound guidance. This is done on both the artery and the vein. The system is preferably placed in the sagittal plane at an angle between 0 and 40 degrees, but preferably between 25 and 40 degrees. In the transverse plane, the system is placed between 0 and 45 degrees, but preferably between 30 and 45 degrees. Many of the connection segments between the graft and the vessel are thought to be unique and should be considered as such for the use of this device without catheters as in open surgical procedures.

The anastomosis device illustratively comprises a tubular graft with first and second ends and a longitudinal passageway extending therethrough. The device further comprises a first stent disposed about the first end of the tubular graft and a second stent disposed about the second end of the tubular graft. In addition, the first stent has hooks or barbs pointed or releasable to point toward the second end of the graft. Similarly, the second stent has at least hooks or barbs pointed or releasable to point toward the first end of the graft. The first and second stents are preferably self-expanding stents such as Z-stents. Alternatively, the stents can be balloon-expandable stents. These stents are resilient stents and comprise preferably nitinol or stainless steel.

The device further comprises an additional stent disposed at least approximately midway along the tubular graft. In addition, the device can comprise a plurality of these additional stents disposed along the graft.

The graft of the present invention comprises a biocompatible material including, for example, an extracellular collagen matrix material, a small intestine submucosa material, a synthetic material or other polymer graft material. The anastomosis device can further comprise an other tubular graft of which the first and second stents are disposed coaxially between the tubular grafts. A slidable collar can also be disposed around an end of the graft to further stabilize the graft within a blood vessel. In addition, the device can further include a surface modification or a coating inhibiting intimal hyperplasia or an exterior coating of a substance that induces homeostasis and includes at least one of fibrin, a fibrin-like substance, and thrombin.

Additionally, the device can include flares at one or more of the ends of the graft.

BRIEF DESCRIPTION OF THE DRAWING

FIG. 2 depicts a pictorial view of a tube of SIS material that can form the inner and outer layers of the anastomosis device of the present invention;

FIG. 3A depicts one end of the anastomosis device of the present invention attached to a vessel;

FIG. 3B depicts the ZILVER stent of FIG. 1A sandwiched between two tubes of SIS material;

FIG. 3C depicts the stent-graft of FIG. 3B with the stent having one or more eyelets at the end thereof;

DETAILED DESCRIPTION

Figure 1A:
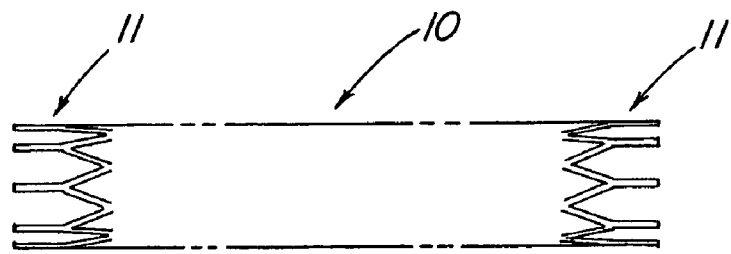
FIG. 1A depicts a side view of a ZILVER® stent with barbs at the ends thereof that is utilized in the anastomosis device of the present invention.

FIG. 1A depicts a side view of a laser cut, modified ZIL-VER® stent 10 with barbs 11 at each end. This stent is utilized in the anastomosis device 12 of the present invention. The ZILVER stent is available from COOK Inc., Bloomington, Ind. The barbs may be cold formed or heat set to fold over or bend down towards the main body of the stent.

Figure 1B:
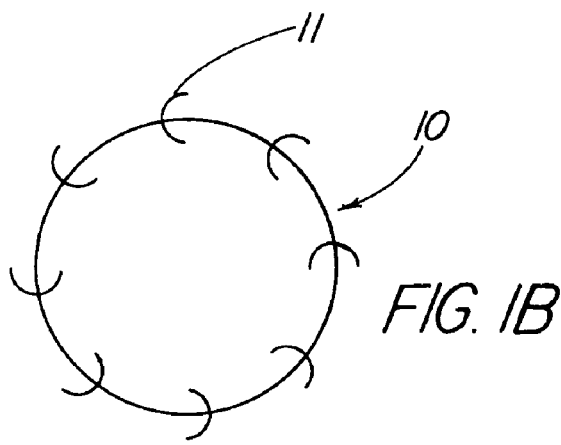
FIG. 1B depicts an enlarged end view of the stent of FIG. 1A from inside an anastomosed vessel.

FIG. 1B depicts an enlarged end view of the ZILVER stent 10 of FIG. 1A from inside a vessel.

Figure 1C:
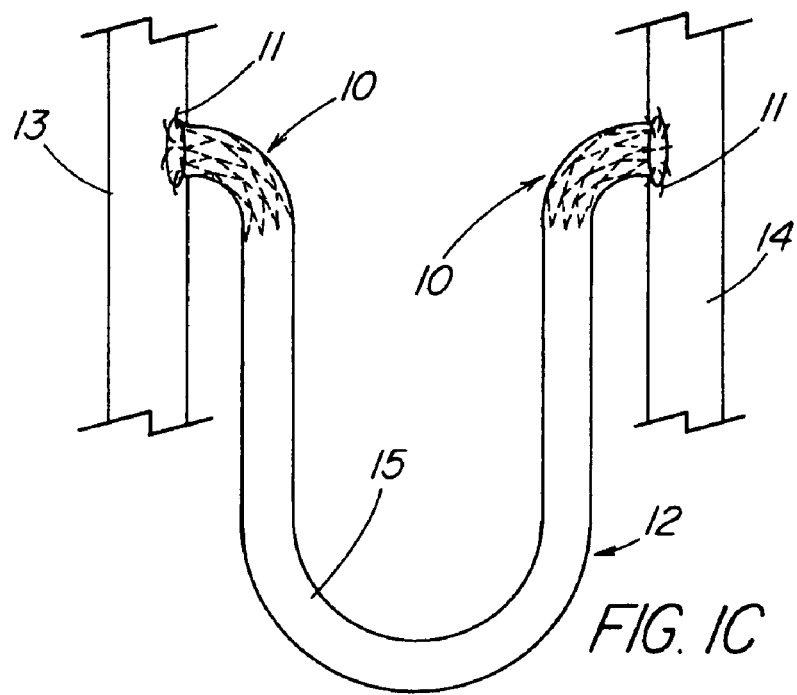
FIG. 1C depicts the anastomosis device of the present invention with the stent of FIG. 1A at each end of a tube of SIS material and connecting an artery and a vein.

FIG. 1C depicts anastomosis device 10 of the present invention attached to artery 13 and vein 14 with ZILVER stents 10 including barbs 11 of FIG. 1A. The device includes first and second stents 10 at first and second ends 47 and 48 of a tube of small intestine submucosa (SIS) material 15.

FIG. 2 depicts a tube 15 of SIS material. This tube is formed from a flat sheet of SIS material sewn with suture material 16 longitudinally therealong to form a tube. Small intestine submucosa (SIS) or another extracellular collagen matrix material is commercially available from COOK Biotech, West Lafayette, Ind. In addition, a small portion of the SIS sheath extends beyond the seam (black lines).

The graft, preferably made of small intestine submucosa, but not limited to commonly used synthetic graft materials, is the conduit that bridges the artery and the vein. At each end of the graft are stents 10 that are preferably made from nitinol and cold formed or heat set at greater than 400 F. The stents are anchored to the inside of the graft wall and provide a retention force when inserted into the blood vessel. The SIS material is preferably vacuum pressed around the stents, rehydrated, and then lyophilized before being placed in the introducer system to provide for optimal compliance. The SIS material must have enough layers, preferably three or more, in the graft to accommodate arterial blood pressure. The layers of SIS material may be adhered together with Fibrin glue. The SIS material may be sewn into a tubular form from a sheet as depicted in FIG. 2. Alternatively, the SIS material may be lyophilized, then slid over the stent or inside the stent. The SIS material may also be vacuum pressed inside the stent or without a stent present, then slid onto or inside the stent.

FIG. 3A depicts one end 17 of another embodiment of the anastomosis device 12 of the present invention attached to vessel 13. End 17 of graft 15 is flared to help maintain the seal of the graft in blood vessel 13. The ends of the graft are preferably flared to an outside diameter greater than the hole in the blood vessel. This should help to form a tight fit and minimize blood loss when the device is advanced into, then pulled back against the inside wall of the blood vessel.

FIG. 3B depicts stent 10 of FIG. 1A sandwiched between first and second tubes 15 of SIS material to form anastomosis device 12. Tubular SIS material is flanged at one end and four barbs 11 of a sandwiched stent penetrate through SIS downwards towards the stent body. The other end is cut to reveal the cross section of the device. Both ends are flanged in the final product.

FIG. 3C depicts anastomosis device 12 of FIG. 3B with stent 10 having one or more eyelets 18.

Figure 4A:
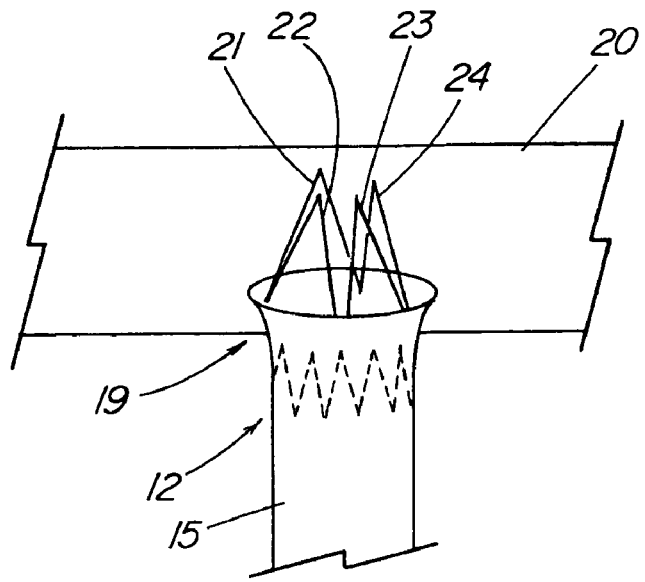
FIG. 4A depicts a side view of one end of the anastomosis device of the present invention being inserted into a vessel.

FIG. 4A depicts a preformed stent 19 at one end of device 12 of the present invention that will open like a flower with petals 21-24, which will hold to vessel wall 20. The stent may be formed at room temperature. The stent may be heat set to fold out at body temperature (e.g. nitinol). The stent may have strings attached at the petals through which follow around the outside of the graft and are pulled by hand outside the body to deploy the stent. The stent may use a percutaneous grabber to hold the tip of each petal or strut at the center of the graft, but can be unlocked by pushing at the proximal end. The stent may consist of Z-stent rings on top of each other. The top Z-stent is placed about half way into the lumen of the blood vessel to which the anastomosis will be made, then opens out like a blossoming flower against the side inside walls of the vessel. Strings pulled from outside the patient or a percutaneous grabber may be used to help deploy the stent.

Figure 4B:
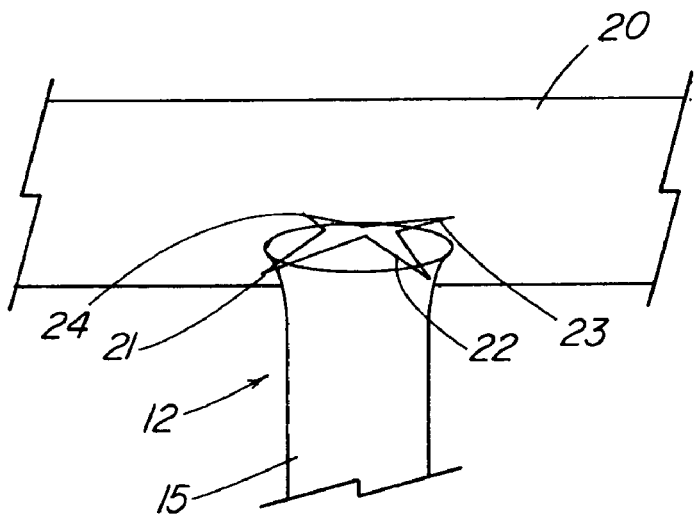
FIG. 4B depicts a side view of one end of the anastomosis device of FIG. 4A with the barbs of the stent folded over and engaging a vessel wall.

FIG. 4B depicts a side view of end 17 of anastomosis device 12 of FIG. 4A with petals 21-24 of stent 19 folded over and engaging a vessel wall 20.

Figure 4C:
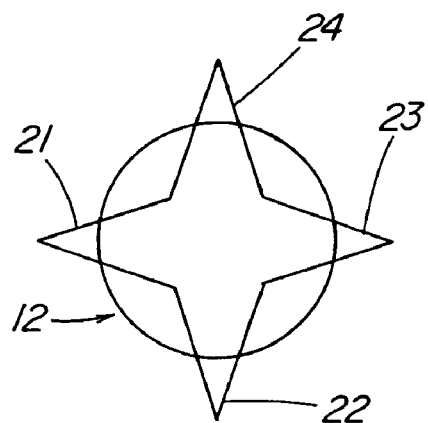
FIG. 4C depicts a top view of the opened anastomosis device of FIG. 4B.

FIG. 4C depicts an end view of an opened anastomosis device 12 of FIG. 4B with petals and barbs 21-24 folded over to engage a vessel wall.

Figure 5A:
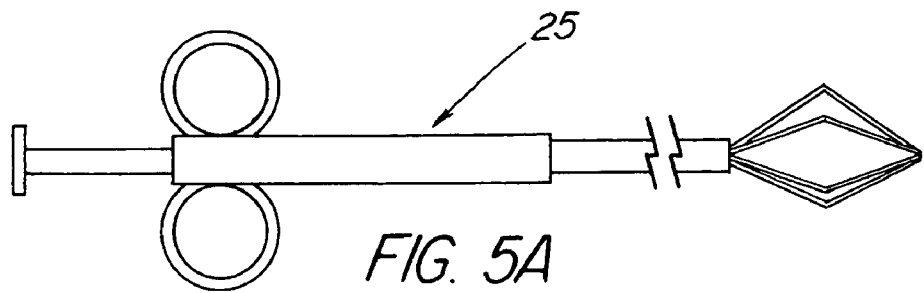
FIG. 5A depicts a percutaneous stent grabber for holding the top stent closed with the strut tips at the center until released.

FIG. 5A depicts a percutaneous stent grabber 25 holding a top stent closed with strut tips at center until released.

Figure 5B:
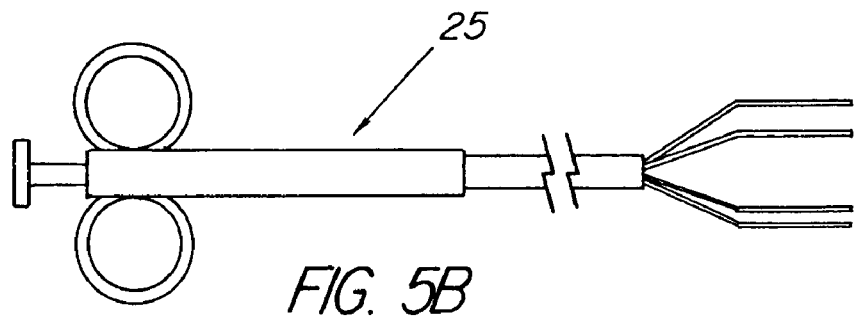
FIG. 5B depicts the stent grabber of FIG. 5A after depression.

FIG. 5B depicts stent grabber 25 of FIG. 5A after depression.

Figure 6A:
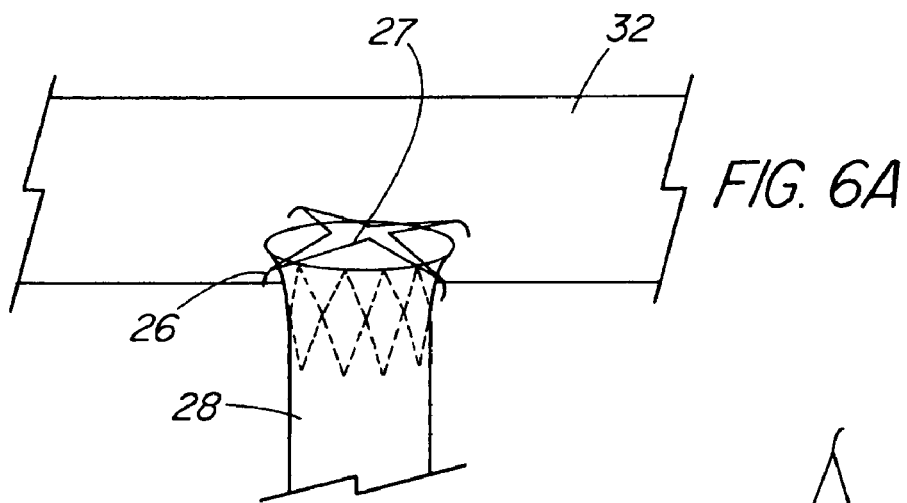
FIG. 6A depicts the deployed anastomosis device of the present invention with the stent of FIG. 1A outside the SIS graft material tube.

FIG. 6A depicts a side view of barbs 26 attached to top stent 27 of anastomosis device 28 to facilitate anchoring into blood vessel 32. The stent may have hooks attached by soldering or laser cut with the stent from cannula that bend down and are parallel to the graft or up to a 45 degree angle from the graft. The hooks may also be attached with a cannula over them and then soldered or laser welded. The hooks may be nitinol or stainless steel.

Figure 6C:
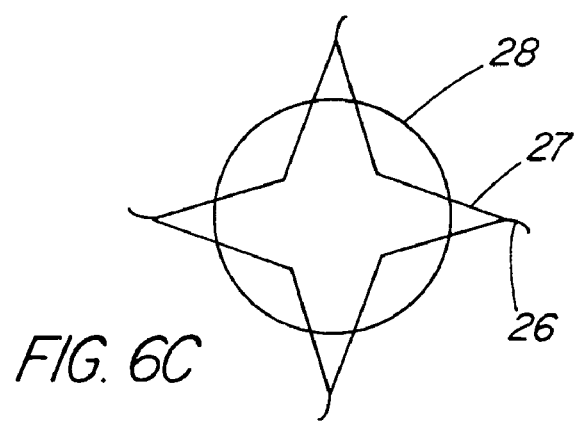
FIG. 6C depicts an end view of the deployed device of FIG. 6A.
Figure 6B:
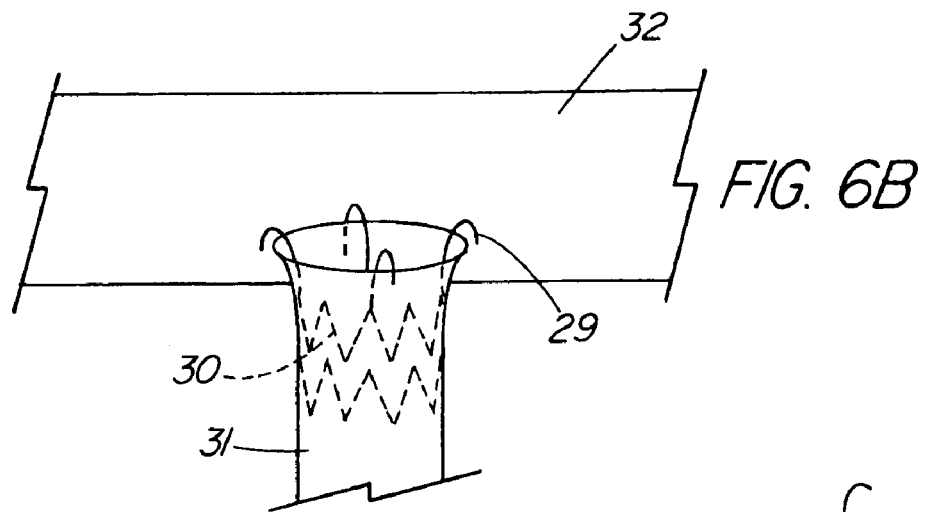
FIG. 6B depicts the anastomosis device of the present invention with the stent barbs placed inside the device.

FIG. 6B depicts formed barbs 29 connected to stent 30 placed inside device 31. Internal stent 30 is a Z-stent or a ZILVER stent.

FIG. 6C depicts an end view of the deployed device of FIG. 6A.

Figure 6D:
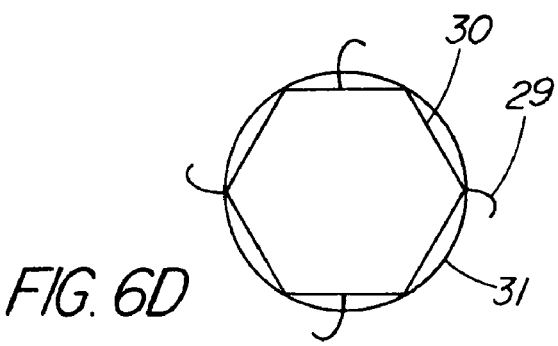
FIG. 6D depicts an end view of the device of FIG. 6B.

FIG. 6D depicts an end view of the deployed device of FIG. 6B.

Figure 7:
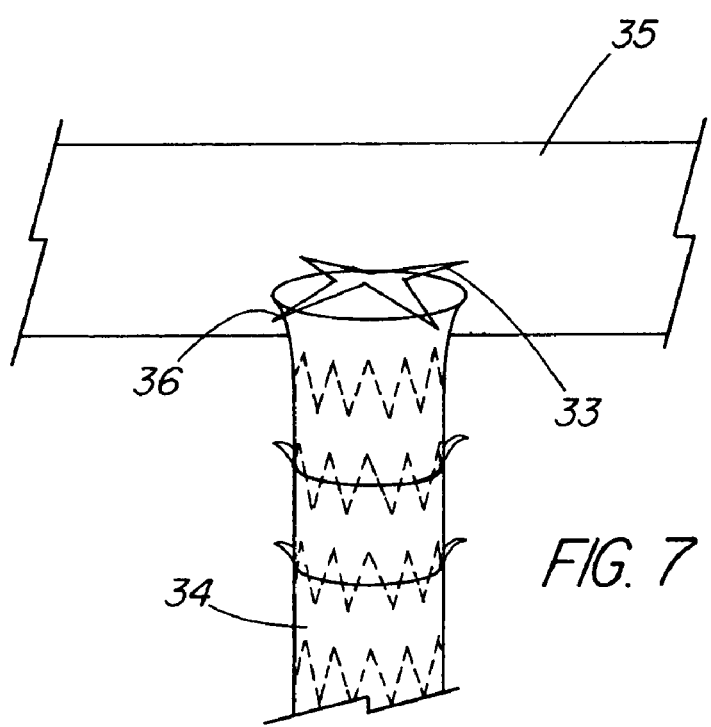
FIG. 7 depicts external barbs positioned on the outside of the anastomosis device of the present invention for maintaining the device against the blood vessel.

FIG. 7 depicts external metal barbs or struts 33 holding graft 34 in place against blood vessel 35. Barbs 33 may be bonded to external stent 36 or attached with a plastic wrap. The device further comprises mechanical anchors to hold the graft against the outside wall of the blood vessel. The anchors pull the stent inside the blood vessel towards the graft and into the wall of the blood vessel and may be employed to further limit dislodgement of the graft. The mechanical anchors help to achieve a normal force to the outside of the roughly perpendicular blood vessel. The mechanical anchors may be achieved by external metal barbs from a stainless steel or nitinol stent wrapped around the outside graft that hold onto subcutaneous tissue and prevents pull out of the graft; a spring loaded stent placed around the outside of the graft that pushes outward in both directions; and a tight fitting collar placed around the outside of each end of the graft and snugged up against the perpendicular vessel to prevent migration of the inside stent.

Figure 8A:
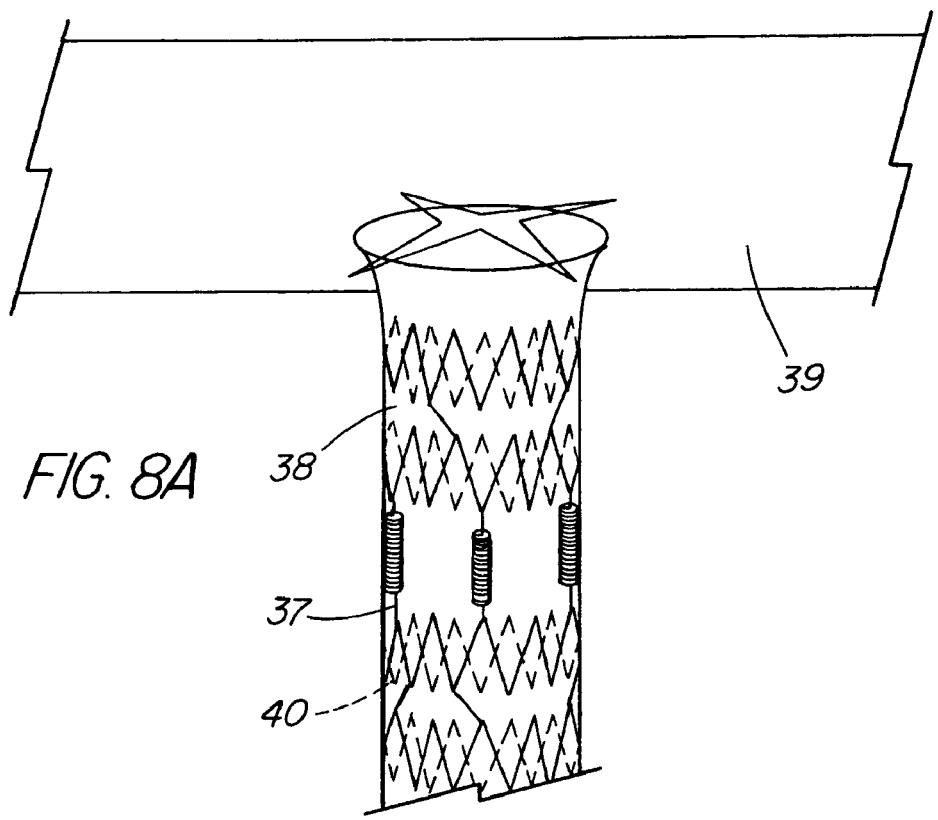
FIG. 8A depicts a spring loaded exterior stent for assisting placement of the graft material of the anastomosis device of the present invention.

FIG. 8A depicts a spring loaded exterior stent 37 prior to deployment to help push graft 38 against vessel wall 39 after deployment.

Figure 8B:
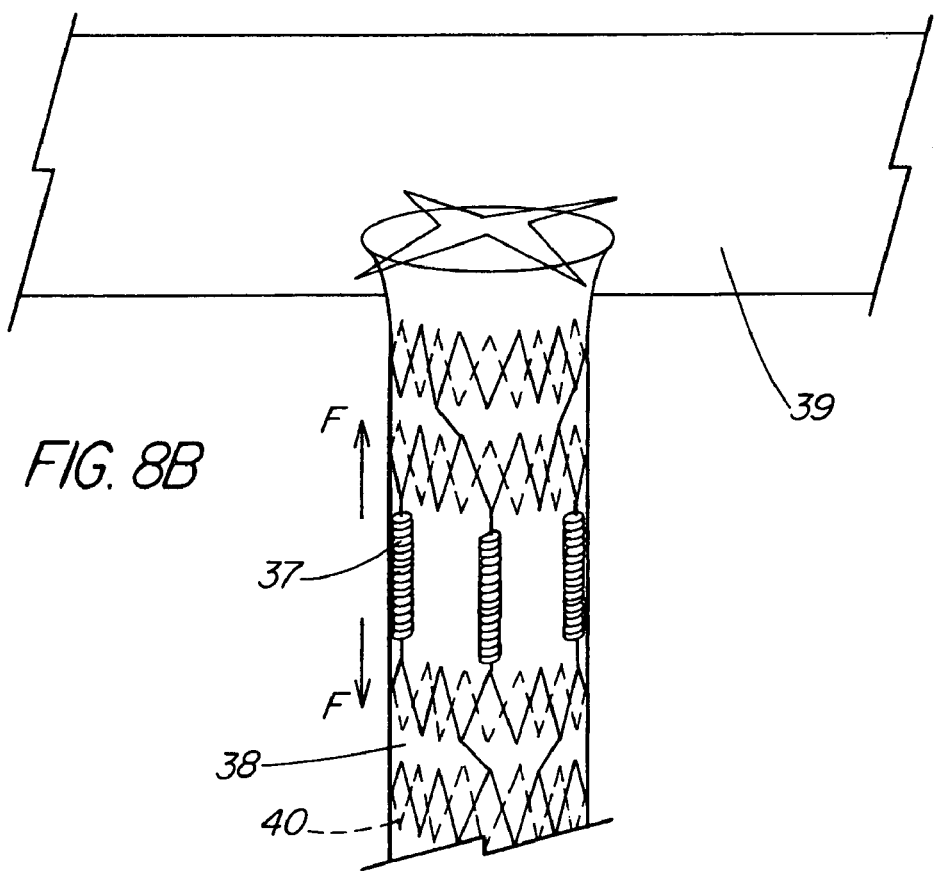
FIG. 8B depicts the anastomosis device of FIG. 8A with the springs deployed.

FIG. 8B depicts the anastomosis device of FIG. 8A with the springs deployed. Dashed marks denote internal stent 40.

Figure 9:
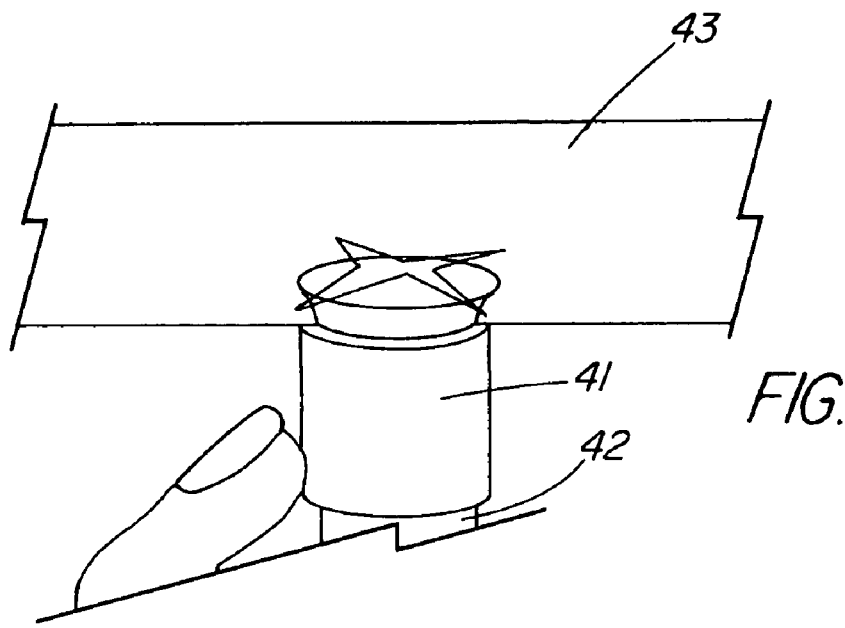
FIG. 9 depicts a collar around the external portion of the anastomosis device of the present invention pushed up against the outside wall of the vessel to secure the graft material against the vessel.

FIG. 9 depicts collar 41 disposed around graft 42 tightly fitted and pushed up against outside vessel wall 43 to secure the graft in place.

Figure 10:
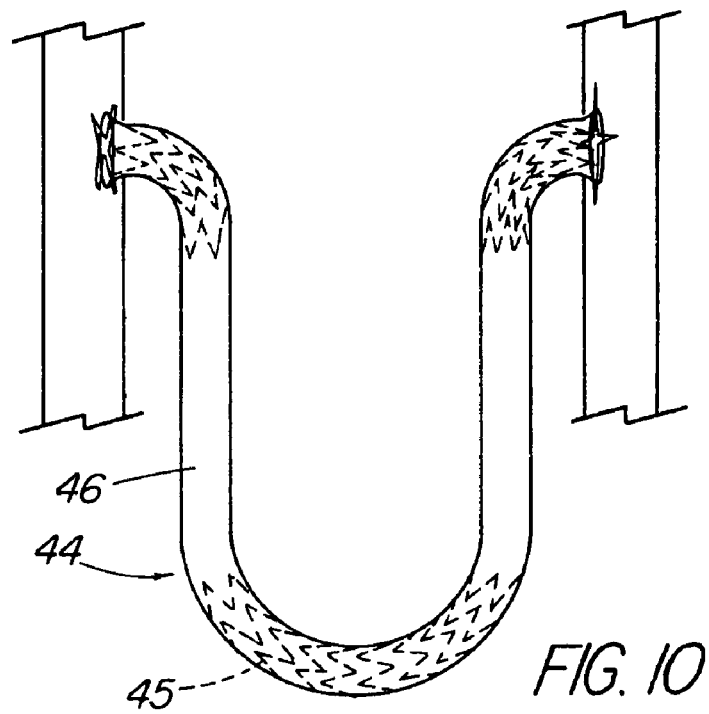
FIG. 10 depicts an anastomosis device of the present invention with an internal stent approximately midway between the graft to minimize kinking.

FIG. 10 depicts an anastomosis device 44 of the present invention with an internal stent 45 midway between graft 46 to minimize kinking. The anastomosis device of the present invention at the middle of the graft is a stent placed to help prevent kinking of the device. These grafts are anchored to the side of an artery, then often extend in a straight section 10 cm before a 180 degree loop. After the loop, another 10 cm straight segment of the graft runs parallel to the first leg and its end is connected to the side of a vein. This invention presents the novel idea of using a stent at the loop portion to prevent kinking. Polytetrafluoroethylene (PTFE), is a commonly used graft material and is not subject to kinking. Most other graft materials, including the preferred material in this invention, SIS, are subject to kinking. The stents of this embodiment are preferably nitinol and of the ZILVER stent geometry, but may be of the Z-stent geometry and also made from stainless steel. The stent may be surface modified and paclitaxel coated too, to limit long term intimal hyperplasia.

The device of the present invention at each end of the graft may also include thrombin, or preferably fibrin or a fibrin-like substance that is applied to the exterior surface of the graft to assist with homeostasis. Fibrin is a naturally occurring substance that, when in contact with blood, causes a platelet plug to form and controls bleeding. Eyelets may also be placed at each bend of the stent or eyelets only at the connection points of the base stent and the top stent to help reduce stress at the bends. Adhesive bonding of the graft around the outside of the base stent may be used by folding the graft from the outside to the inside, gluing, then cutting off any excess.

What is claimed is:

1. An anastomosis device comprising:
   a tubular graft having a first end, a second end, and a longitudinal passageway from the first end to the second end;
   a spring-loaded stent device attached to the tubular graft and comprising a first stent, a second stent, and one or more springs connected to the first and second stents;
   where the springs bias the first stent towards the first end of the graft and the second stent towards the second end of the graft.

2. The anastomosis device of claim 1, further comprising a third stent disposed at the first end of the tubular graft and a fourth stent disposed at the second end of the tubular graft, where the third and fourth stents each have at least two petals configured to fold over the respective graft end to engage an inside surface of a blood vessel.

3. The anastomosis device of claim 2, where the petals of the third stent have at least one of hooks and barbs pointed or releasable to point toward the second end of the graft and where the petals of the fourth stent have at least one of hooks and barbs pointed or releasable to point toward the first end of said graft.

* * * * *